United States Patent [19]

Liebig et al.

[11] Patent Number: 4,517,687
[45] Date of Patent: May 21, 1985

[54] SYNTHETIC WOVEN DOUBLE-VELOUR GRAFT

[75] Inventors: William J. Liebig, Hohokus, N.J.; Dennis Cummings, County Claire, Ireland

[73] Assignee: Meadox Medicals, Inc., Oakland, N.J.

[21] Appl. No.: 418,149

[22] Filed: Sep. 15, 1982
(Under 37 CFR 1.47)

[51] Int. Cl.³ .............................. A61F 1/00; A61F 1/24
[52] U.S. Cl. ............................................ 3/1.4; 428/36;
428/229; 428/257; 428/258; 428/259
[58] Field of Search ............... 428/36, 229, 257, 258, 428/259; 3/1.4

[56] References Cited

U.S. PATENT DOCUMENTS

| | | | |
|---|---|---|---|
| 3,561,441 | 2/1971 | Lombardi | 128/156 |
| 3,878,565 | 4/1975 | Sauvage | 3/1.4 |
| 4,047,252 | 9/1977 | Liebig et al. | 3/1.4 |
| 4,209,859 | 7/1980 | Hoffman | 128/334 R |

*Primary Examiner*—James J. Bell
*Attorney, Agent, or Firm*—Blum, Kaplan, Friedman, Silberman & Beran

[57] ABSTRACT

A woven double-velour fabric of synthetic fiber provides an excellent structure for ingrowth and adhesion of tissue thereto and can be woven tightly enough so that preclotting may be omitted is so desired. The features recited are achieved through the use of appropriate combinations of preshrunk, texturized yarn with unshrunk, untexturized yarn.

13 Claims, 3 Drawing Figures

U.S. Patent    May 21, 1985    4,517,687
FIG.1
FIG.2
FIG.3
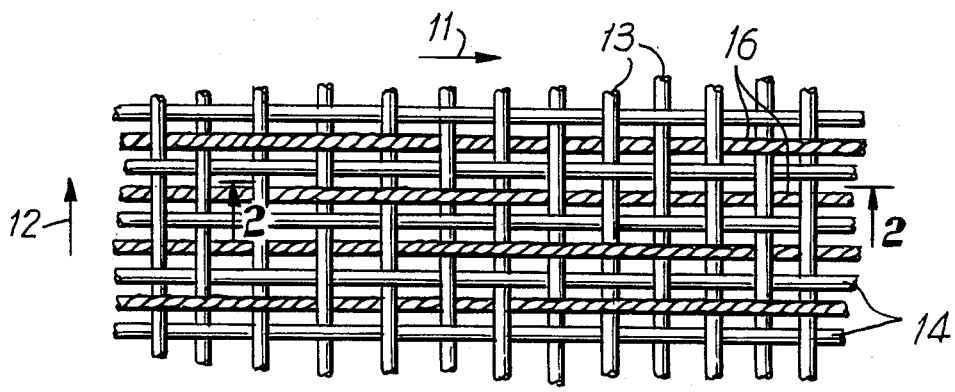
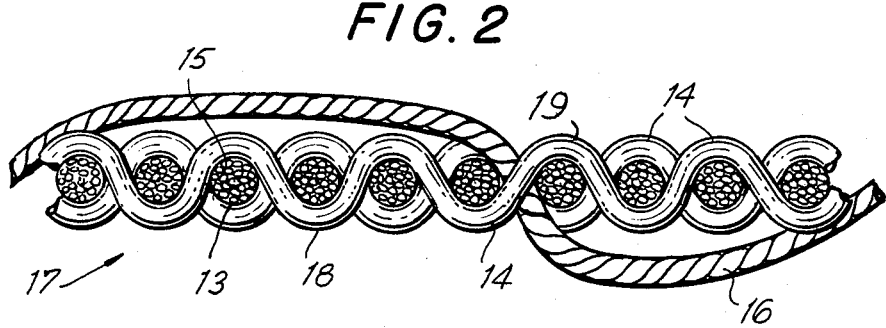
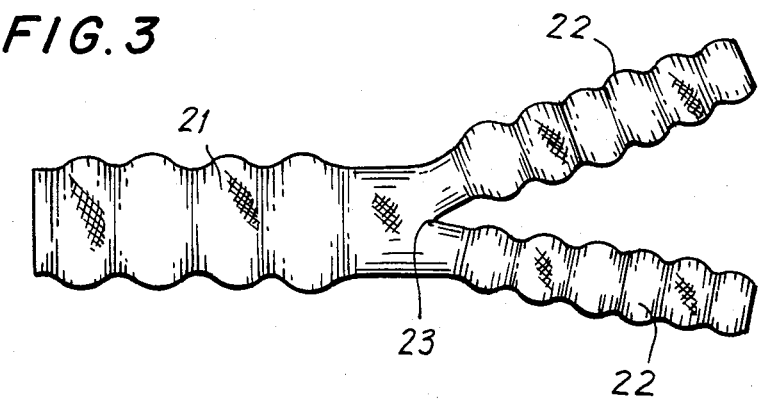

SYNTHETIC WOVEN DOUBLE-VELOUR GRAFT

BACKGROUND OF THE INVENTION

Vascular grafts of sythetic fiber are now widely used, a variety of constructions and a variety of materials being available. A principal factor in selection of a particular graft is the porosity of the fabric of which the graft is composed. This factor is significant because the porosity controls both the tendency to hemmorrhage and the ingrowth of tissue into the wall of the graft.

The general procedure for implantation of a graft includes the step of preclotting, a step in which the graft is immersed in the blood of the patient after which the graft is allowed to stand for a period long enough for clotting to ensure. As a result, when the graft is implanted surgically, hemmorrhaging does not occur; yet, growth of tissue into the wall of the graft can proceed. This growth is extremely important, since, eventually, the wall of the graft simulates the wall of the vessel which it replaces and, if all goes properly, provides a lumen which remains open and free of clots.

The degree of adhesion of tissue to the wall of the graft varies with the material used. Thus, V. J. Lombardi in U.S. Pat. No. 3,561,441 discloses the use of a non-sticking material having loops thereon for use in covering and treating wounds. The material which he proposes to use is a polyfluorinated polyolefin filament, spun on a plastic ribbon form. Lombardi discloses that, as a result of the non-stick property, the fabric can be removed from a wound periodically as a step in the changing of the dressing without tearing open the wound itself. Obviously, such a material is not suitable for use where the material is to remain within the body.

L. R. Sauvage in U.S. Pat. No. 3,878,565 has disclosed a tubular textile synthetic cardio-vascular prothesis of polyester or other synthetic fiber, the prothesis consisting of a body having a multiplicity of fiber loops extending outwardly from the surface thereof. Also, as shown in his FIG. 2A, the body is crimped into irregular, circumferential corrugations. Such corregations are intended to provide protection against kinking or collapse of the tubing and narrowing of the lumen thereof as a result of bending or other factors. However, the degree of protection afforded by such irregular corrugation varies over the lengths of the tube and can be below the required level of protection at specific regions.

While the construction of Sauvage facilitates growth of tissue exterior to the body or trellis of the tubular graft, the absence of loops on the interior of the tubing may result in exposure of the synthetic filaments of which the tubing is composed. Furthermore, the Sauvage graft is circularly-knit so that the technique which provides the fabric loops in the Sauvage graft is not applicable to woven tubing.

Liebig et al in U.S. Pat. No. 4,047,252 have described a synthetic vascular graft which is warp-knit from a fiber or filament to which growing tissue can adhere. The preferred fiber is stated to be polyester, and an especially preferred fiber is that sold under the trade name of Dacron by Dupont. As is well known, Dacron is polyethylene terephthalate. The Liebig et al fabric, while presenting an excellent substrate for ingrowth of tissue is sufficiently porous so that preclotting is generally necessary in the use of this material. Woven fabrics, in general, have lower porosities than do knit fabrics, whether warp-knit or circularly knit, but do not present so suitable a structure for tissue ingrowth. Thus, while woven fabrics of very low porosity are available, they are not so suitable for tissue ingrowth as are the double velours, namely, those having velour loops on both the inner and outer surfaces of the fabric.

As is evident, it would be desirable that graft fabric whether tubular or flat, have low porosity and facilitate the growth of tissue along both the interior and exterior surfaces thereof.

SUMMARY OF THE INVENTION

A synthetic graft material is woven from a fiber or filament to which growing tissue can adhere. A preferred fiber is polyester, and an especially preferred fiber is that sold under the trade name of Dacron by Dupont. However, it is to be understood that any comparable fiber or yarn is to be included as a suitable alternate or substitute. Further, the scope of the invention is to be considered as including combinations of different fibers, such combinations presenting advantages due to differences in shrinkage during compaction.

In order to facilitate growth of tissue through and over both surfaces of fabric in accordance with the present invention, fiber loops are provided on both surfaces. Where the fabric is in the form of tubing, loops are provided on the interior as well as on the exterior thereof.

Where the fabric is in the form of tubing, in order to avoid interference with the flow of blood in the lumen of said tubing, the fiber loops on the interior thereof are shorter, i.e., smaller than those on the exterior thereof. The ratio of the length of the interior loops to the length of the exterior loops may be described as x/y, where x varies from 1 to 4 and y varies from 5 to 8.

In the preparation of the fabric of the present invention, both preshrunk, texturized yarn and unshrunk, untexturized yarn are utilized. The warp is comprised of both types of yarn, and the fill may be of the unshrunk, untexturized yarn alone or may be used in combination with preshrunk, texturized yarn, the two types of yarn being twisted together (in the fill only) prior to weaving. The method of preshrinking and texturizing the yarn is well known to those skilled in the art.

A preferred weave is as follows:
Warp: 1/70/54 (5z)+2/40/27 texturized, preshrunk.
Fill: 1/70/54 (5z)+2/40/27 texturized preshrunk (1.5s).
Pattern: 070/205/6/4, 30 dent/reed, 8 ends/dent.
Greige count: 64 picks/in., 122≠10% ends/in., off of the loom.

The aforenoted describes the loom set-up for weaving double-velour grafts, in accepted terminology.

Subsequent to weaving, the fabric is compacted as described in U.S. Pat. No. 4,209,859, column 3, line 18. The principal features of the graft in accordance with the present invention result from the fact that the preshrunk, texturized yarn of which the loops are composed shrinks far less during compaction than does the unshrunk, untexturized material. As a result, the fabric is compacted in both the warp and the fill directions, while the loops of the preshrunk material shrink far less or not at all during the compaction process. This difference in shrinkage causes loops to stand out from the body of the fabric which may be termed a trellis.

Where the fabric is in tubular form, it is generally crimped to eliminate the danger of kinking or collapse of the tubing at any point. Bifurcated grafts may also be prepared, the grafts may be viewed as having three legs coming together at a crotch. All three legs are preferably crimped. In the immediate region of the crotch the bifurcated graft may be either crimped or uncrimped.

In order to ensure that the loops will stand out from the trellis, the texturized yarn is fed at higher rate than is the untexturized yarn. In addition, the texturized yarn is fed at lower tension.

Accordingly, an object of the present invention is a method of preparing a closely woven, double-velour fabric of a material to which tissue can adhere, and which provides an optimum combination of low porosity and rapid tissue ingrowth.

Another object of the present invention is a closely woven double-velour synthetic vascular graft and graft material to which tissue can adhere readily.

A further object of the present invention is a method of preparing a closely woven double-velour, synthetic vascular graft wherein loops on the exterior of said fabric extend outwardly further than loops on the interior of said fabric extend inwardly. A significant object of the present invention is a method of preparing a closely-woven double-velour synthetic vascular graft in which the graft is compacted and corrugated and has uniform strength throughout.

A particularly important object of the present invention is a closely-woven double-velour synthetic vascular graft and graft material which provides for rapid tissue ingrowth and which is of a porosity low enough so that pre-clotting may be avoided.

Still other objects and advantages of the invention will in part be obvious and will in part be apparent from the specification.

The invention accordingly comprises the several steps and the relation of one more of such steps with respect to each of the others, and the article possessing the features, properties, and the relation of elements, which are exemplified in the following detailed disclosure and the scope of the invention will be indicated in the claims.

BRIEF DESCRIPTION OF THE DRAWINGS

For a fuller understanding of the invention, reference is had to the following description taken in connection with the accompanying drawings in which:

FIG. 1 is a closely-woven, double-velour fabric prepared in accordance with the present invention;

FIG. 2 is a view taken along line 2—2 of FIG. 1; and

FIG. 3 is a view of a circumferentiallly-crimped, bifurcated vascular graft in accordance with the present invention.

DESCRIPTION OF THE PREFERRED EMBODIMENTS

To prepare for the weaving of a graft fabric in accordance with the present invention, yarn is first preshrunk and texturized, using techniques well known to those skilled in the art. The preferred yarn material is polyethylene terephthalate, available from Dupont under the trade name of Dacron. A suitable yarn is two-ply, 40 denier with twenty-seven filaments to each ply. However, yarn which is either heavier or lighter than 40 denier and which contains more or less than 27 filaments per bundle may be used.

In weaving the fabric, the warp must contain both the preshrunk, texturized yarn and unshrunk untexturized yarn. the two yarns are independent of each other, i.e., they are not twisted together. It is significant that in subsequent treatment of the fabric (the compaction step) the unshrunk, untexturized yarn will shrink substantially whereas the texturized, preshrunk material will change in length, only slightly, if at all. The fill may consist of unshrunk, untexturized yarn alone or, preferably, consists of both unshrunk, untexturized yarn and preshrunk, texturized yarn. The two yarns are twisted together prior to weaving. The preferred weave for the fabric is described as follows:

Warp: 1/70/54 (5z)+2/40/27 texturized, preshrunk.
Fill: 1/70/54 (5z)+2/40/27 texturized, preshrunk (1.5s).
Pattern: 070/205/6/4, 30 dent/reed, 8 ends/dent.
Greige count: 64 picks/in., 122≠10% ends/in., off of the loom.

It should be noted that the warp must include both the preshrunk texturized yarn and the unshrunk untexturized yarn; the fill may consist of untexturized, unshrunk yarn alone.

A fabric in accordance with the present invention is shown in FIG. 1 in which the warp direction is shown by the arrow 11 and the fill direction is indicated by the arrow 12. The fill yarns 13 are shown in FIG. 1 as being spaced apart for convenience in representation. However, in general, the fill yarns 13 are woven as tightly as possible with warp yarns 14. The yarns indicated by reference numeral 13 are to be considered as representing either unshrunk, untexturized yarn twisted together with preshrunk, texturized yarn or the unshrunk, untexturized yarn by itself. The yarns indicated by the reference numeral 14 are the unshrunk, untexturized material and the yarns indicated by the reference numerals 16 are the preshrunk, texturized material.

In the weaving process, yarn 16 is fed at a higher rate and at lower tension than is feed yarn 14. Control of the ratio of feed rates and tensions makes it possible to adjust the size of the loops forming the velour and the ratios of the lengths on the two faces of the fabric. In general, the rate of feed and the tensions are adjusted to achieve ratios which may be described as x/y, with x, the length of the loops on the interior being 1 to 4 and y, the length of the loops on the exterior, being 5 to 8. The absolute lengths of the loops depend on the relative rates at which the trellis yarn or yarns and the warp yarns are fed. Where the fabric is woven in tubular form, the shorter loops are on the interior of the tubes and the longer loops are on the exterior thereof.

FIG. 2 which is a view taken along line 2—2 of the FIG. 1 and shows fill yarns 13, each yarn 13 consisting of filaments 15. As aforenoted, fill yarns 13 may consist of unshrunk, untexturized material alone or of the two types of yarn twisted together, that is, both the preshrunk and unshrunk yarns. Fill yarn 13 is tightly interwoven with warp yarn 14 which is the untexturized material. Also, loosely interwoven with fill 13 is loop yarn 16 which is the preshrunk, texturized yarn. In the pattern shown in FIG. 2, the interior 18 of the fabric is the lowermost side and the exterior 19 is the uppermost side.

As shown in FIG. 2, interior loop 16 passes under four fill yarns and passes over six fill yarns. Two of these loop yarns are shown in FIG. 1 and are indicated by the reference numeral 16. As will be noted, adjacent warp loops need not pass over and pass under the same fill yarns. Thus, a variety of patterns becomes available and easily made.

After weaving, the fabric, whether flat or woven in tubular form, is compacted. The method of compaction is described in U.S. Pat. No. 4,209,859, or other suitable means may be used. The compaction is an extremely important step in that the unshrunk, untexturized yarn shrinks substantially while the preshrunk texturized yarn shrinks very little during this treatment with the result that the loops of the preshrunk material stand out from the two surfaces of the fabric.

An extremely important use of the fabric is as a vascular graft. For this purpose, the fabric must be woven in tubular form, either straight, or bifurcated. In either form, it is desirable that the fabric be circumferentially crimped in order to prevent kinking or collapse of the lumen at any point along the tubes. A bifurcated is shown in FIG. 3 in which both the larger and the smaller-diameter tubes, indicated by the reference numerals 21 and 22 are crimped, except in the immediate vicinity of crotch 23, the three legs of the vascular graft being in the form of a Y. In general, the diameters of legs 22 are substantially less than the diameter of main tube 21.

Tests have shown that the porosity of the woven double-velour is not quite as low as that of a woven fabric prepared with an untexturized warp. While the very lowest porosity is desirable so far as hemmorrhaging is concerned, a fabric woven with the untexturized warp does not provide so advantageously for growth of tissue through the trellis as does the woven double-velour described herein. Accordingly, the combination of relatively low porosity with both interior and exterior loops on the surfaces of the fabric is such that pre-clotting may be omitted if desired while yielding an excellent substrate for tissue ingrowth.

What is claimed is:

1. A tightly-woven, low-porosity prosthesis, to which tissue can adhere, comprising:
    a woven double-velour fabric material formed from a warp yarn and a fill yarn and having loops formed from loop yarns about the fill yarns, the yarns being of a yarn material to which growing tissue can adhere;
    the warp yarn being one of untexturized, unshrunk yarn and texturized, shrunk yarn, said fabric having loops of said texturized yarn on both surfaces thereof for facilitating adherence of tissue to said prosthesis.

2. The tightly-woven, low-porosity, prosthesis of claim 1, wherein said fill yarn is untexturized and unshrunk.

3. The tightly-woven, low-porosity prosthesis of claim 1, wherein said fill yarn is texturized, preshrunk yarn twisted together with untexturized, unshrunk yarn.

4. The tightly-woven, low-porosity prosthesis of claim 1, wherein said woven fabric has been compacted.

5. The tightly-woven, low-porosity, prosthesis of claim 4, wherein said woven fabric is in tubular, circumferentially-crimped form.

6. The tightly-woven, low porosity prosthesis of claim 5, wherein said tubular form is in the form of a Y, having three legs and a crotch at the junction of the legs, said woven fabric being uncrimped in the region immediately proximate said crotch and crimped over the remainder thereof.

7. The tightly-woven, low-porosity prosthesis of claim 5, wherein said fabric in said tubular form has both internal and external loops, the ratio of the lengths of said internal to said external loops being x/y, where x is 1 to 4 and y is 5 to 8.

8. The tightly-woven, low porosity prosthesis of claim 5, wherein said warp has the specification 1/70/54 (5z)+2/40/27 of texturized and preshrunk yarn and said fill has the specification 1/70/54 (5z)+2/40/27 of the woven prosthesis texturized and preshrunk (1.5s) yarns.

9. The tightly-woven, low porosity, prosthesis of claim 5, wherein the pattern of said woven fabric is 070/205/6/4, 30 dent/reed, 8 ends/dent.

10. The tightly-woven, low-porosity, prosthesis of claim 5, wherein the greige count of said fabric is 64 picks/in., 122=10% ends/in., off of the loom.

11. The tightly-woven, low-porosity, prosthesis of claim 1, 2, 3, 4, 5, 6, 7, 8, 9 or 10, wherein said material is polyethylene terephthalae.

12. A woven double-velour synthetic vascular prosthesis, comprising:
    a tubular fabric of texturized preshrunk polyethylene terephthalate yarns, said fabric having an interior surface and an exterior surface;
    said fabric woven from warp yarns and fill yarns and having loops of loop yarns about the fill yarns extending from the interior surface and exterior surface, wherein the ratio of the length of the interior loops to the exterior loops varies from 1 to 4.

13. The vascular prosthesis of claim 12, wherein the tubular fabric has been compacted.

* * * * *